United States Patent [19]

Meyerhoff et al.

[11] Patent Number: 4,694,834
[45] Date of Patent: Sep. 22, 1987

[54] GAS SENSOR

[75] Inventors: Mark E. Meyerhoff, Ann Arbor, Mich.; Eric J. Fogt, Maple Grove; Darrel F. Untereker, Cedar, both of Minn.

[73] Assignee: Medtronic, Inc., Minneapolis, Minn.

[21] Appl. No.: 846,388

[22] Filed: Mar. 31, 1986

[51] Int. Cl.$^4$ .............................................. A61B 5/00
[52] U.S. Cl. ................... 128/635; 204/403; 204/431
[58] Field of Search ............... 128/635; 204/403, 415, 204/431, 432

[56] References Cited

U.S. PATENT DOCUMENTS

| 4,273,636 | 6/1981 | Shumada et al. | 204/415 |
| 4,312,332 | 1/1982 | Zick | 128/635 |
| 4,409,980 | 10/1983 | Yano et al. | 128/635 |
| 4,534,355 | 8/1985 | Potter | 128/635 |

Primary Examiner—Lee S. Cohen
Attorney, Agent, or Firm—Grady J. Frenchick; Joseph F. Breimayer; John L. Rooney

[57] ABSTRACT

A simplified gas sensor which includes a pH sensitive transducer having a gate-insulated field effect transistor (FET) structure. The gas sensor is particularly adapted to detect carbon dioxide in fluids.

11 Claims, 8 Drawing Figures

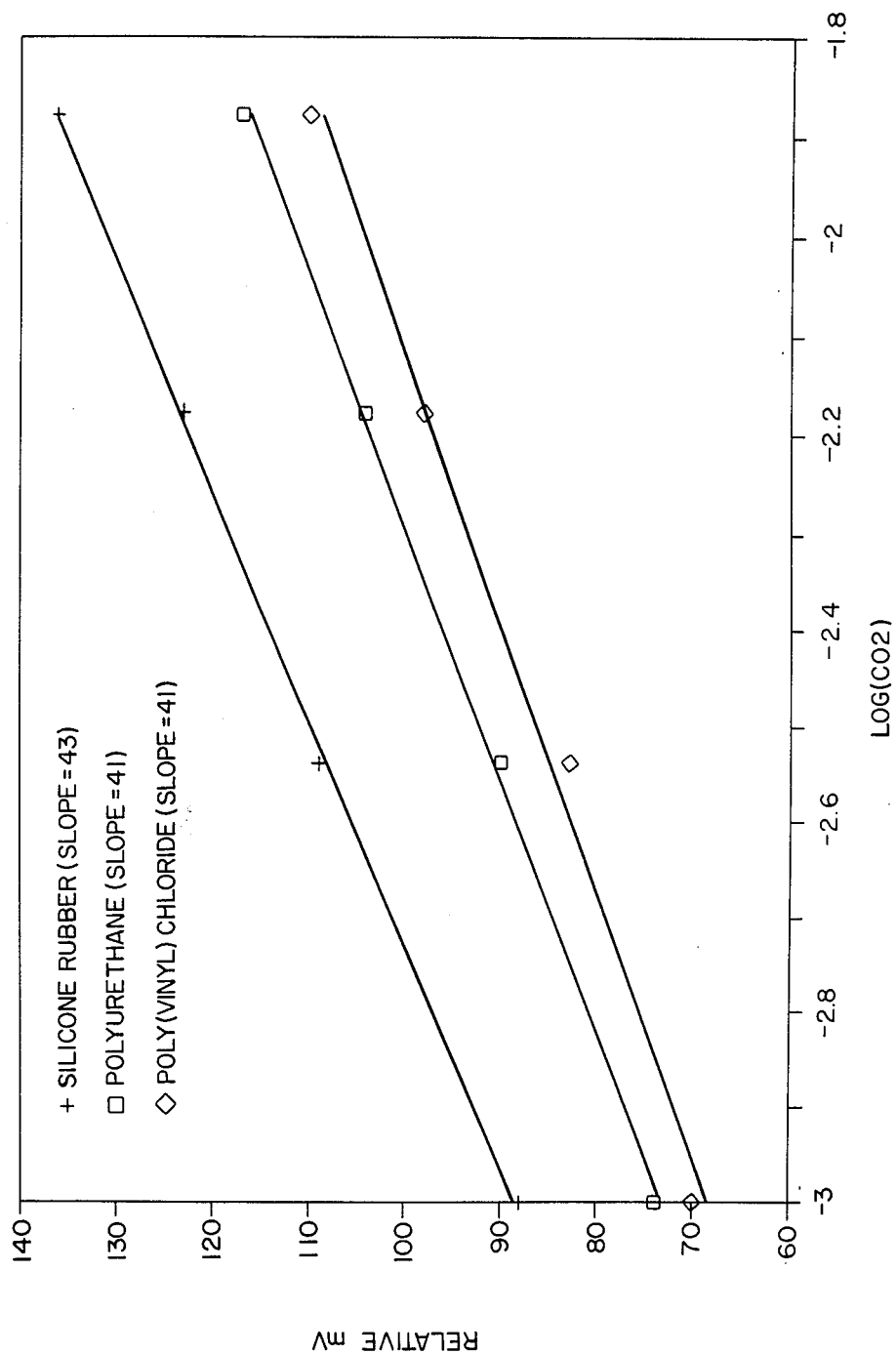

GAS SENSOR

BACKGROUND OF THE INVENTION

1. Field of the Invention

This invention relates to gas sensors. More particularly, this invention relates to gas sensors, particularly for carbon dioxide ($CO_2$) or ammonia ($NH_3$). Even more particularly, this invention relates to $CO_2$ gas sensors employing a pH sensitive, T. gate-insulated, field effect transistor transducer (FET).

2. Description of the Prior Art

The measurement of gas concentration in fluid media (i.e., gas or liquid) has been the subject of much recent research. Particularly, in the medical field, there exists a need for a miniature, reliable, stable device for in vivo measurement of the concentration of $CO_2$ in body fluids such as venous or arterial blood or intercellular fluid. This need is discussed by Fogt et al in "Response of Ion-Selective Field Effect Transistors to Carbon Dioxide and Organic Acids", *Anal. Chem.* 1985, 57, 1995-1998. U.S. Pat. No. 4,409,980 to Yano et al, which is incorporated by reference herein, discloses such a device. U.S. Pat. No. 4,474,183 also discloses a FET gas sensor which is of the related, Severinghaus type.

The above-mentioned '980 patent discloses a gas sensor comprising a reference electrode deposited on the surface of a pH-sensitive transducer having a gate-insulated field-effect transistor (FET) structure and adjacent a gate region of the FET, the transducer and reference electrode being housed in a flexible tube so that the gate region of the FET is located in an opening provided at the front end of or on the side wall of the tube, lead wires connected to the FET and to the reference electrode and which extend along the tube, electrical insulation resin filling the space between the inner wall of the tube and lead-wire-FET joints to stop the opening of the tube, an electrolyte-containing hydrophilic polymer layer stretching at least over both the FET gate region and a part of the reference electrode and a gas permeable membrane placed over the polymer layer.

The present invention is a gas sensor of the type described in the '980 patent which is simpler and, therefore, easier to fabricate.

SUMMARY OF THE INVENTION

Briefly, in one aspect of the present invention is a gas sensor comprising a pH-sensitive FET transducer having a gate-insulated field-effect transistor structure, a reference electrode optionally deposited on the surface of said transducer and adjacent the gate region of said transducer, an insulating tube which provides connecting lead wires to the FET transducer and to the reference electrode (if present) and which houses said transducer and reference electrode, said gate region of said FET transducer being located in the opening provided in said insulating tube, said lead wires extending along said insulating tube and electrical insulation resin placed between the inner wall of said tube and lead-wire-FET connecting points to stop said opening of the tube and a gas permeable membrane overlying and in direct contact with the gate region of the FET transducer and the reference electrode (if present) so as to preclude the presence of a polymeric layer therebetween.

Of critical importance to the present invention is the fact that contrary to the explicit teaching and claims of Yano et al in the '980 patent, the present invention is a workable, miniaturizable, gas sensor (particularly for $CO_2$) which has eliminated the complication of an electrolyte-containing hydrophilic polymer layer between the FET gate region and the overlying gas permeable membrane. This is surprising and unexpected and is contrary to the teaching of Yano et al.

BRIEF DESCRIPTION OF THE DRAWINGS

FIG. 7 is a calibration curve for the response (in mV) for three sensors of this invention at various carbon dioxide concentrations in aqueous media.

DETAILED DESCRIPTION OF THE INVENTION

The chemistry of FET-based carbon dioxide sensors is set forth in the Yano et al '980 patent at column 1, line 38 to 70 and column 2, lines 1 through 67 which discussion is incorporated by reference herein. As with the gas sensor of Yano et al, while the present invention preferably contemplates the detection of carbon dioxide, particularly in body fluids, the concentration of other gases such as ammonia may be determined. The primary structural change that would be needed to detect gases other than $CO_2$ (as described below), would be to select a membrane which is selectively permeable to such other gases.

The structural features which this invention has in common with the device of the Yano '980 patent are described in the Yano et al '980 patent at columns 5 and 6 and lines 1 through 6 of column 7. The following description of the common features is based on the Yano '980 description.

Figure 1:
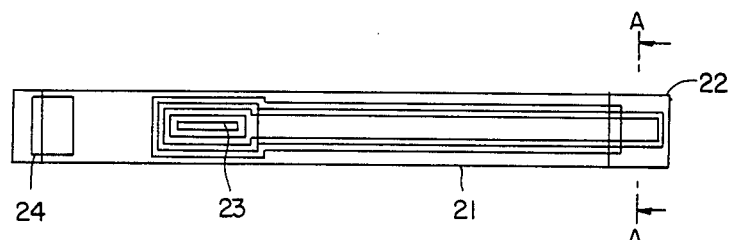
FIG. 1 is a plan view showing a pH sensitive FET transducer employed in the gas sensor of the present invention.
Figure 2:
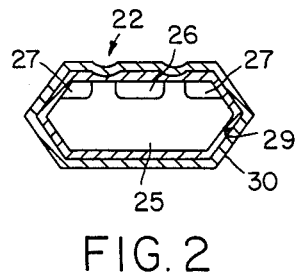
FIG. 2 is a section taken on line A—A in FIG. 1.

Referring to the drawings, FIG. 1 is a plan view showing a pH sensitive FET transducer 21 employed in the gas sensor of the present invention. The FET transducer 21 generally has an elongated configuration, for example, 0.4 mm wide and 3-4 mm long, and is provided with a gate region 22 at one end and a drain terminal 23 and a source terminal 24 at the other end or adjacent thereto. For detailed construction of such FET transducer, reference is made to U.S. Pat. No. 4,218,298 which discloses a selective chemical sensitive FET transducer. As can be seen from FIG. 2 which shows a section taken on line A—A in FIG. 1, the gate region 22 has a drain diffusion region 26 and a source diffusion region 27, both formed on a silicon substrate 25, the entirety of the gate region 22 being covered with two layers, that is, an oxidized layer 29 and a surface stabilizing layer 30 laid thereon. Surface stabilizing layer 30 may be of silicon nitride ($Si_3N_4$), alumina ($Al_2O_3$) or tantalum pentoxide ($Ta_2O_5$). A sensor having such a layer is sensitve to hydrogen ion.

Figure 3:
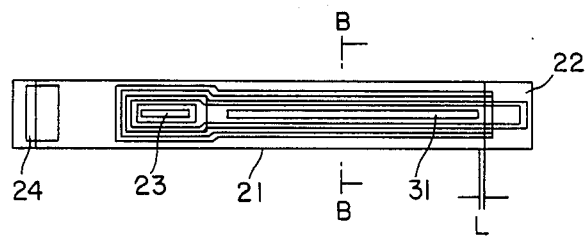
FIG. 3 is a top plan view showing a reference electrode deposited on the surface of the FET transducer in FIG. 1.

FIG. 3 is a plan view showing a reference electrode 31 which is optionally deposited on the substrate of FET transducer 21 in close relation to the gate region 22 of the FET.

Figure 4:
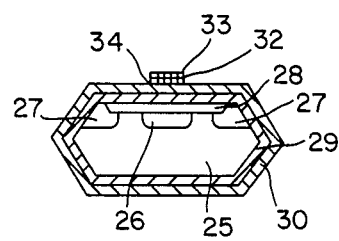
FIG. 4 is a section taken on line B—B in FIG. 3.

As shown in FIG. 4 which is a section taken on line B—B in FIG. 3, the reference electrode 31 is formed of silver (Ag) 32 and silver chloride (AgCl) 33, for example. Such Ag-AgCl layer may be formed by vacuum evaporation, electrolytic metal plating and electrolytic chlorination. Usually with known FET gas sensors, an Ag-AgCl layer is deposited on a FET substrate without provision of a bonding layer between. Generally, however, silver does not form a good bond with surface stabilizing layer 30 in the FET transducer. Therefore, it is desirable to provide, between the silver layer and the surface stabilizing layer, a bonding layer 34 which will form a good bond with both of said layers. If the surface stabilizing layer is of silicon nitride, such materials as chromium, chrome copper and nickel may be suitable for use as bonding layer 34. Shown at 28 is a channel stopper layer. The thickness of the bonding layer 34 and Ag-AgCl layers, 32,33 on the silicon nitride layer 30 has great bearing upon both stability and serviceability of the sensor. Therefore, the thickness of the bonding layer 34 provided on the silicon nitride layer 30 is preferably 100–1,000 Å. If the thickness of the bonding layer is not more than 100 Å, the bonding layer will not provide any sufficient bond. A thickness greater than 1,000 Å provides no advantage worthy of the length of time required in depositing the bonding layer; rather, it will make the layer liable to separate. Silver layer 32 and silver chloride layer 33 on the bonding layer should not be made too thin. Unreasonably thin silver and silver chloride layers will be a cause of unstable measurement or severe drift and will render the sensor unserviceable, though the sensor may work properly just after manufacture thereof. Therefore, to ensure good serviceability of the sensor, the thickness of the silver layer is preferably more than $3 \mu$ and that of silver chloride layer is preferably more than $1 \mu$. Formation of a Ag-AgCl layer may be performed, for example, by thinly depositing a chrome layer over the $Si_3N_4$ layer on the FET, placing thereon a silver layer by vacuum evaporation or electrolytic metal plating, then subjecting the layers to electrolysis in a NaCl solution, with the deposited Ag as anode, so that the silver layer surface is chlorinated. Thus, an Ag-AgCl reference electrode is formed. In order to provide a relatively thick silver layer, it is desirable that a thin silver layer be formed by vacuum evaporation, then a sufficiently thick silver layer be formed thereon by electrolytic metal plating.

Figure 5:
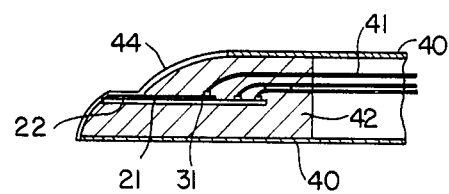
FIG. 5 is a fragmentary sectional view of a gas sensor of this invention.

FIG. 5 is a fragmentary sectional view showing a construction of a gas sensor of the invention. The pH sensitive FET transducer 21 has a substrate on which is deposited the reference electrode 31 shown in FIGS. 3 and 4. The transducer 21 is housed in a flexible insulation tube 40 or, for example, the front portion of a catheter, of such material as polyethylene, polypropylene, polytetrafluoroethylene, silicon, nylon 11, polyvinyl chloride, or polyethelene terephthalate, with its gate region 22 exposed in the front opening of the insulation tube 40. Individual lead wires 41 connected to the reference electrode 31 and FET transducer 21 are insulation-coated and passed through the insulation tube, with their ends drawn out of the rear end of the tube. For the purpose of protecting the FET transducer 21 from breakage, the front opening of the insulation tube 40 extends beyond the front end of the transducer. Further, said front opening is diagonally cut away so that it is easily insertible into a living body. The space between the FET transducer 21, reference electrode 31, lead-wire-FET joints and the inner wall of the insulation tube is packed with electrical insulation resin 42, such as epoxy resin or silicone resin, whereby the front portion of the insulation tube is stopped.

Electrical insulation resin 42 is packed in the tube, except for the front opening, and the space occupied by the FET gate region and a part of the reference electrode to stopper the tube.

As alluded to above, the present gas sensor contemplates the presence of a reference electrode. In one practice of this invention, the reference electrode can be located as described above, i.e., adjacent the gate region of the pH sensitive FET structure. However, it is to be noted that the actual location of the reference electrode in the practice of this invention is not critical and could be located other than shown and described in FIGS. 3–5. Thus, for example, the reference electrode could be located separately or apart from the rest of the sensor structure.

Overlying and in direct contact with reference electrode 21 and gate 22 so as to preclude the presence of a distinct layer therebetween, is gas permeable polymer 44. It is this polymer 44 which is selectively permeable to e.g., $CO_2$, so as to permit the device to detect the presence of $CO_2$ in fluids.

In the Yano et al '980 patent there is described a hydrophilic polymer layer containing electrolyte which is liable to pH variation, this polymer electrolyte layer being disposed between gas permeable polymer 44 and the rest of the sensor structure, particularly the gate region 22 and the reference electrode 31. The surprising and unexpected nature of this invention is that such a hydrophilic polymer layer has been found not to be necessary. This simplifies the present invention from that of Yano and thus making it easier to construct.

Figure 6:
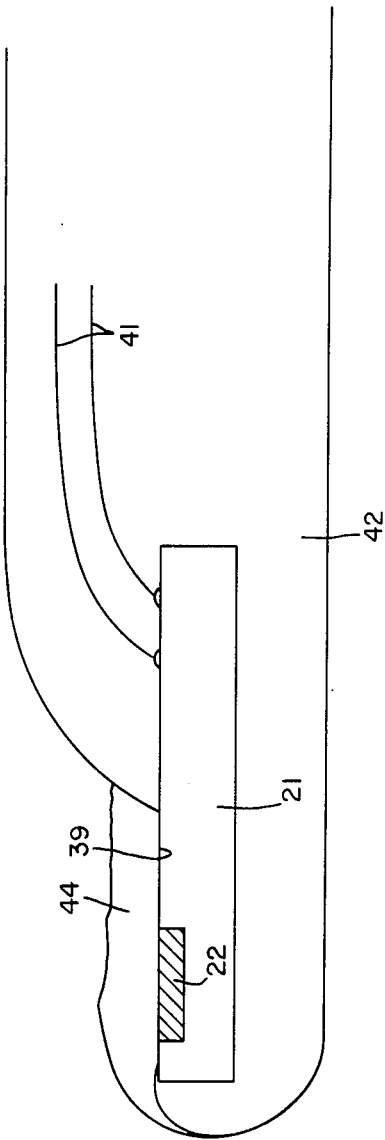
FIG. 6 is an enlarged schematic representation of a sensor of this invention in cross section.

The present invention is more clearly depicted in FIG. 6 which is an enlarged schematic of the structure shown in FIG. 5 with the reference electrode and some of the other features omitted for clarity. Shown in FIG. 6 is FET transducer 21, gate region 22, lead wires 41, electrical insulation 42 and gas permeable polymer 44. As is clearly shown in FIG. 6, there is no hydrophilic polymer layer between gas permeable polymer 44 and the rest of the FET structure. The intersection 39 precludes the presence of a visible layer therebetween.

For the purpose of this polymer 44, known gas-permeable, polymeric membranes may be used. Among known membranes as such are fluoroplastics which are polymers and copolymers of polytetrafluoroethylene, trifluoroethylene, hexafluoropropylene, chlorotrifluoroethylene and the like, and polyolefin polymers, e.g., polyvinyl chloride (PVC), polyethylene, polypropylene, polypentene-1, urethane materials and the like. Membrane thickness is generally a balance of response time and strength. Useful membrane thicknesses fall in the range of $3\mu$ to $300\mu$, also depending upon the material selected.

For the purpose of coating the gas permeable membrane on the pH sensitive FET structure, various methods such as dip coating, spray coating, vacuum evaporation, ultraviolet photo-polymerization, plasma polymerization and sputtering may be used. To ensure satisfactory response speed, the gas permeable membrane must be uniform and thin. More especially, polymers, such as polytetrafluoroethylene, polyethylene, and polypropylene, must be of thin configuration; and for this purpose, use of a vapor-phase polymerization method, such as vacuum evaporation, ultraviolet photo-polymerization, plasma polymerization, or sputtering, is preferred. It is also possible to have a gas-permeable tube, the front end of which is closed, laid over the gate region of the sensor, with the other end of the tube fixed liquid-tightly to the sensor. This method is particlarly preferred for a sensor having an elongated configuration, because it permits miniaturization.

The gas sensor of the present invention may be manufactured in the following manner:

(1) Optional reference electrode 31, if it is to be so located, is deposited on the surface of pH-sensitive FET transducer 21 (FIG. 1) in manner as shown in FIG. 3.

(2) Lead wires 41 are connected to reference electrode 31 and FET transducer 21, and peripheral area is insulated with epoxy resin. FET transducer 21 is housed in catheter 40, with gate region 22 of transducer 21 disposed in front opening of catheter 40. Thereafter, epoxy resin 46 is filled in between lead-wire-FET joints and the inner wall of the catheter to stop the front portion of the catheter.

(3) Gas-permeable membrane 44 is then placed over the gate region 22 of transducer 21 and over optional reference electrode 31 to complete manufacture of the device.

A gas sensor so manufactured will not work in its as manufactured state as such. So, it must be subjected to moisture pickup and swelling in water or vapor before it is actually used.

For example, it is necessary to soak the freshly prepared sensor in an aqueous environment for a period of time needed to condition it. The length of the period of time which the sensor must be conditioned is variable and depends upon the particular gas permeable membrane selected, its thickness and the temperature at which it is conditioned. The time period for soaking generally falls in the range of 1 hour to 24 hours.

It has also been found that the sensitivity of the present sensor can be enhanced if a film of bicarbonate is deposited on top of the pH sensitive gate region prior to laying down the gas permeable membrane, a suitable bicarbonate layer may be deposited by dipping the pH FET in an aqueous sodium bicarbonate solution (0.1 to 1.0M) and evaporating the water in air. Any method that results in deposition of a small amount of bicarbonate on the pH sensitive FET surface would be usable herein.

FIG. 7 depicts calibration curves for sensors of the present invention as shown in FIGS. 1–6 and as described above. These calibration curves show the sensitivity of sensors of this invention to various concentrations of carbon dioxide in an aqueous environment. The horizontal axis of FIG. 7 is, as shown, in units of $-\log [CO_2]$ while the vertical axis is in relative mV output. Relative mV were employed so that the various outputs could be displayed on a single figure. This representation was chosen because the absolute voltages of the various sensors are quite different. Also indicated in FIG. 7 is that different gas permeable membranes provide different slopes on the concentration vs. output plot. The materials which were employed as the gas permeable polymer (44) to produce the plots were, from top to bottom, silicone rubber, polyurethane and polyvinyl chloride.

Figure 8:
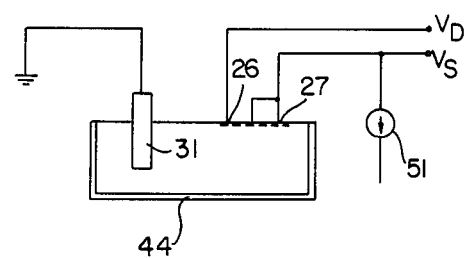
FIG. 8 is an electrical circuit diagram incorporating a gas sensor of this invention.

Measuring operation with the sensor is performed through the circuit shown in FIG. 8. The circuit shown is a source follower circuit. The reference electrode is grounded. A constant voltage $V_D$ is applied to drain 26. A constant current flows between drain 26 and source 27 via constant current circuit 51. As it passes through gas-permeable membrane 44, gas changes the surface potential of gate region 22 of the FET transducer 21 exposed to the membrane 44. The change in surface potential is followed by a change in source potential $V_S$. Accordingly, by measuring potential between output terminal 52 and reference electrode 31, it is possible to determine hydrogen ion concentration on the surface of the gate region of the pH-sensitive FET transducer, that is, gas concentration in the solution.

What is claimed is:

1. A gas sensor comprising:
   a pH-sensitive FET transducer having a gate-insulated field-effect transistor structure;
   a reference electrode;
   an insulating tube having an opening which provides connecting lead wires to the FET transducer and which houses said transducer, said gate region of said FET transducer being located in the opening provided in said insulating tube, and said lead wires extending along said insulating tube;
   electrical insulation resin placed between the inner wall of said tube and lead-wire-FET connecting points to stop said opening of the tube; and
   a gas permeable membrane overlying and in direct contact with the gate region of the FET transducer whereby the existence of any discernible layer between the gas permeable membrane and the FET transducer is precluded.

2. The gas sensor of claim 1 wherein the surface of said gate region of the pH-sensitive FET transducer is covered with a layer of silicon nitride, alumina, tantalum pentoxide or tantalum nitride.

3. The gas sensor of claim 1 wherein said pH-sensitive FET transducer has an elongated configuration with said gate region located at the front end thereof and an electrode region at the opposite end.

4. The gas sensor of claim 1 wherein the opening provided in the insulating tube is located at the front end of the tube or on the side wall thereof.

5. The gas sensor of claim 1 or 4 wherein said insulating tube is a flexible slender tube capable of being inserted into a living body.

6. The gas sensor of claim 1 wherein said reference electrode is deposited on the surface of said transducer and adjacent the gate region thereof.

7. The gas sensor of claim 6 wherein said reference electrode comprises a silver layer deposited on the surface of the FET transducer and a silver chloride layer formed thereon.

8. The gas sensor of claim 6 wherein a bonding layer is provided between the substrate of the FET transducer and the silver layer.

9. A gas sensor according to claim 6 wherein the gas permeable membrane is selected from the group consisting of polyvinyl chloride, urethane polymers or silicone rubber.

10. The gas sensor of claim 9 wherein the gas-permeable membrane is a silicon membrane having a thickness in the range of 30–300 microns.

11. The gas sensor of claim 1 wherein the gas-permeable membrane is selected from the group consisting of polyvinyl chloride, urethane polymers or silicone rubber.

* * * * *

UNITED STATES PATENT AND TRADEMARK OFFICE
CERTIFICATE OF CORRECTION

PATENT NO. : 4,694,834

DATED : September 22, 1987

INVENTOR(S) : Meyerhoff et al

It is certified that error appears in the above—identified patent and that said Letters Patent are hereby corrected as shown below:

Column 1,
    Line 10, after "sensitive,", delete "T.".

Column 6, claim 8, line 54, "6" should be "7".

Signed and Sealed this

Tenth Day of May, 1988

Attest:

DONALD J. QUIGG

Attesting Officer

Commissioner of Patents and Trademarks